(12) United States Patent
Fernandez

(10) Patent No.: US 9,858,361 B2
(45) Date of Patent: Jan. 2, 2018

(54) RECONFIGURABLE GARMENT DEFINITION AND PRODUCTION METHOD

(71) Applicant: Dennis S. Fernandez, Atherton, CA (US)

(72) Inventor: Dennis S. Fernandez, Atherton, CA (US)

(*) Notice: Subject to any disclaimer, the term of this patent is extended or adjusted under 35 U.S.C. 154(b) by 503 days.

(21) Appl. No.: 14/589,854

(22) Filed: Jan. 5, 2015

(65) Prior Publication Data

US 2015/0120253 A1    Apr. 30, 2015

Related U.S. Application Data

(63) Continuation of application No. 13/454,390, filed on Apr. 24, 2012, now Pat. No. 8,930,012, which is a continuation of application No. 12/540,954, filed on Aug. 13, 2009, now Pat. No. 8,185,231, which is a continuation of application No. 12/238,336, filed on Sep. 25, 2008, now abandoned, which is a continuation of application No. 11/027,819, filed on Dec. 29, 2004, now Pat. No. 7,522,970.

(51) Int. Cl.
| | |
|---|---|
| G06F 17/50 | (2006.01) |
| A41H 3/00 | (2006.01) |
| A61B 5/00 | (2006.01) |
| G06Q 30/06 | (2012.01) |
| A41D 1/00 | (2006.01) |
| A61B 5/02 | (2006.01) |
| A61B 5/024 | (2006.01) |
| A61B 5/08 | (2006.01) |
| A61B 17/00 | (2006.01) |

(52) U.S. Cl.
CPC ............ *G06F 17/50* (2013.01); *A41H 3/007* (2013.01); *A61B 5/0002* (2013.01); *A61B 5/6804* (2013.01); *G06Q 30/0601* (2013.01); *A41D 1/002* (2013.01); *A61B 5/02* (2013.01); *A61B 5/024* (2013.01); *A61B 5/0816* (2013.01); *A61B 2017/00017* (2013.01); *A61B 2017/00084* (2013.01); *A61B 2017/00212* (2013.01); *Y02T 10/82* (2013.01); *Y10S 2/905* (2013.01)

(58) Field of Classification Search
CPC ... G06F 17/50; A61F 3/07; A61F 3/04; A61B 5/6824; A61B 5/6804; A61B 5/6806
USPC .................................................. 700/130–138
See application file for complete search history.

(56) References Cited

U.S. PATENT DOCUMENTS

| | | |
|---|---|---|
| 2,856,466 A | 10/1958 | Gustafson et al. |
| D207,919 S | 6/1967 | Fai |
| D212,863 S | 12/1968 | Roberts |

(Continued)

FOREIGN PATENT DOCUMENTS

TW        93137997        12/2004

OTHER PUBLICATIONS

Can a dress replace a doctor? Will we wear buildings? Will clothing replace computers? . . . , Blog, Nov. 2003 <http://anettegustafsson.blogs.com/netsky/files/TechnoFashion.pdf>.

(Continued)

*Primary Examiner* — Danny Worrell
(74) *Attorney, Agent, or Firm* — Dennis Fernandez

(57) ABSTRACT

Computer-aided design and manufacture software and hardware automate garment and fashion definition and production. Configurable garment includes ornamental element, pattern display, and personal identifier and wireless sensor electronics.

15 Claims, 4 Drawing Sheets

(56) References Cited

U.S. PATENT DOCUMENTS

| | | | |
|---|---|---|---|
| 3,769,663 | A | 11/1973 | Perl |
| 4,283,127 | A | 8/1981 | Rosenwinkel et al. |
| 4,578,709 | A * | 3/1986 | Lang .................... G02B 26/101 345/55 |
| 4,683,587 | A | 7/1987 | Silverman |
| 4,856,086 | A | 8/1989 | McCullough |
| 4,882,769 | A | 11/1989 | Gallimore |
| 5,020,150 | A | 5/1991 | Shannon |
| 5,404,385 | A | 4/1995 | Ben-Haim |
| 5,414,405 | A | 5/1995 | Hogg et al. |
| 5,495,568 | A | 2/1996 | Beavin |
| 5,563,951 | A | 10/1996 | Wang et al. |
| 5,568,126 | A | 10/1996 | Andersen et al. |
| 5,745,034 | A | 4/1998 | Andersen et al. |
| 5,757,661 | A | 5/1998 | Surville |
| 5,768,135 | A | 6/1998 | Park et al. |
| 5,850,222 | A | 12/1998 | Cone |
| 6,010,216 | A | 1/2000 | Jesiek |
| 6,023,241 | A | 2/2000 | Clapper |
| 6,031,511 | A * | 2/2000 | DeLuca .................... G09G 3/22 345/55 |
| 6,046,712 | A | 4/2000 | Beller et al. |
| 6,091,546 | A | 7/2000 | Spitzer |
| 6,091,832 | A | 7/2000 | Shurman et al. |
| 6,150,998 | A | 11/2000 | Travers et al. |
| 6,198,394 | B1 | 3/2001 | Jacobsen et al. |
| 6,246,994 | B1 | 6/2001 | Wolven et al. |
| 6,278,425 | B1 * | 8/2001 | DeLuca .................... G09G 3/22 345/55 |
| 6,281,788 | B1 | 8/2001 | Noll |
| 6,349,001 | B1 | 2/2002 | Spitzer |
| 6,408,330 | B1 | 6/2002 | DeLaHuerga |
| 6,409,338 | B1 | 6/2002 | Jewell |
| 6,415,199 | B1 | 7/2002 | Liebermann |
| 6,435,386 | B2 | 8/2002 | Scott |
| 6,473,671 | B1 | 10/2002 | Yan |
| 6,474,367 | B1 | 11/2002 | Jayaraman et al. |
| 6,483,483 | B2 | 11/2002 | Kosugi et al. |
| 6,516,240 | B2 | 2/2003 | Ramsey et al. |
| 6,545,606 | B2 | 4/2003 | Piri et al. |
| 6,546,309 | B1 | 4/2003 | Gazzuolo |
| 6,564,118 | B1 | 5/2003 | Swab |
| 6,654,046 | B2 | 11/2003 | Eccleshall |
| 6,725,124 | B2 | 4/2004 | Yan |
| 6,729,726 | B2 | 5/2004 | Miller et al. |
| 6,769,767 | B2 | 8/2004 | Swab et al. |
| 6,874,127 | B2 | 3/2005 | Newell et al. |
| 6,882,897 | B1 | 4/2005 | Fernandez |
| 6,911,172 | B2 | 6/2005 | Swab et al. |
| 6,929,365 | B2 | 8/2005 | Swab et al. |
| 6,966,647 | B2 | 11/2005 | Jannard et al. |
| 7,013,009 | B2 | 3/2006 | Warren |
| 7,039,486 | B2 | 5/2006 | Wang |
| 7,147,324 | B2 | 12/2006 | Jannard et al. |
| 7,231,038 | B2 | 6/2007 | Warren |
| 7,242,999 | B2 | 7/2007 | Wang |
| 7,445,332 | B2 | 11/2008 | Jannard et al. |
| 7,461,936 | B2 | 12/2008 | Jannard |
| 2001/0043164 | A1 | 11/2001 | Thagard et al. |
| 2002/0004763 | A1 | 1/2002 | Lam |
| 2002/0021297 | A1 | 2/2002 | Weaver |
| 2002/0039170 | A1 | 4/2002 | Jannard et al. |
| 2003/0011590 | A1 | 1/2003 | Kung et al. |
| 2003/0151118 | A1 | 8/2003 | Baude et al. |
| 2003/0152691 | A1 | 8/2003 | Baude et al. |
| 2003/0196239 | A1 | 10/2003 | Zic et al. |
| 2003/0208830 | A1 | 11/2003 | Marmaropoulos et al. |
| 2003/0212319 | A1 | 11/2003 | Magill |
| 2003/0214408 | A1 | 11/2003 | Grajales et al. |
| 2003/0215632 | A1 | 11/2003 | Jen |
| 2004/0029582 | A1 | 2/2004 | Swab et al. |
| 2004/0078285 | A1 | 4/2004 | Bijvoet |
| 2008/0204440 | A1 | 8/2008 | Swain |
| 2012/0204310 | A1 | 8/2012 | Fernandez |

OTHER PUBLICATIONS

Grant, Glenn. "Smart Fabrics." Freelance Traveller [online], Jun. 6, 2003 [retrieved on Nov. 22, 2003]. <http://www.freelancetraveller.com/features/consgoods/smartfab.html>.

Davis, Robert, "Smart T-shirts' know when something is wrong Applications abound, from babies at home to soldiers at war," USA Today.com, Nov. 17, 1998.

Power Dressing Could Spark a Trend, globaltechnoscan.com [online], Mar. 2003 [retrieved on Nov. 22, 2003]. <http://www.globaltechnoscan.com/22ndMarch-28thMarch/power.htm>.

Sondhi, Anjali. "Invention: Key to Survival," Imagesfashion.com [online], Jun. 2003, [retrieved on Nov. 22, 2003]. <http://www.imagesfashion.com/back/june/innovations.htm>.

Johnson, R.Colin. "Nano research eyes ink jet-printed 'sheets' of circuits." EETimes [online], Nov. 20, 2003 [retr. Nov. 20, 2003] <http://www.eet.com/story/OEG20031120S0017>.

Mokhoff, Nicolas. "OLED contracts go to military suppliers." EETimes [online], Nov. 11, 2003 [retrieved on Nov. 12, 2003]. <http://www.eet.com/story>.

Intelligent Clothing Website. Intelligent Clothing [online], Nov. 2003 [retrieved on Nov. 22, 2003]. Retrieved from: <http://www.intelligentclothing.com/introduction.htm>.

Space, textile and information technologies: a unique combination of expertise for development of a new generation of communicating . . . , Virtual Medical Worlds (Oct. 2002).

Lymberis, A., and Olsson, S."Smart biomedical clothes promising way to keep the European citizen healthy," Virtual Medical Worlds (Jul. 31, 2002).

Goettling, Gary, "Building the Future: Weaving Technology into Shirts," gtalumni.org [online], Nov. 2003. From: <http://gtalumni.org/StayInformed/magazine/win00/building.html>.

Wearable Computers in the Medical Profession, Tomorrows Technology for Teachers [online], Dec. 1999. <http://ed.tsud.edu/tcubed/cool_tech/Wearable_Computers_Medical.htm>.

Body Handles Nanofiber Better, Technology Review [online], Dec. 2003 [retr. on Dec. 22, 2003]. Retrieved from: <http://www.technologyreview.com/articles/rnb_121503.asp>.

Wood, Lamont, "Weaving new functions into fashion," Chicago Tribune Online Edition, Oct. 28, 2002.

Where fabrics meet electronics, SOFTswitch Media Release [online], Nov. 2003 [retr. on Nov. 22, 2003]. Retrieved from <http://www.softswitch.co.uk/SOFTswitchMediaRelease.html>.

Verma, S.S., "Wearable Electronic clothes," The Tribune Online Edition, Chandigarh, India, Nov. 20, 2003.

Marculescu, et al., "Ready to Ware," IEEE Spectrum Online, Nov. 22, 2003.

Post, et al., "Smart Fabric, or Washable Computing," in Digest of Papers of the First IEEE Symposium on Wearable Computers (Oct. 13-14, 1997), pp. 167-168.

2003 IEDM Technical Program, 2003 IEEE International Electron Devices Meeting (Oct. 2003).

Rudolf Tromp to receive the Davisson-Germer Prize, IBM Research News, Oct. 2003.

Krane, Jim, "Telltale Clothes," CBSNews.com, Mar. 2003, New York.

Eisenberg, Anne. "For the Smart Dresser, Electric Threads That Cosset You", The New York Times, Feb. 6, 2003, p. G. 7.

Ruibal, Sal. "Winter Coat Packs Its Own Thermostat", USA Today, Mar. 14, 2002, Sports, p. 16c.

Wearable technology, textiles, fashion and other semi-related topics. Styleborg: Fashion Archives [online], Nov. 2003 [retr. on Nov. 22, 2003]. <http://styleborg.com/2003/11>.

Piquepaille, Roland. "'Smart' Clothing: A fashion Show." Roland Piquepaille's Fashion Trends [online], Oct. 13, 2003 [retr. on Nov. 22, 2003]. <http://radio.weblogs.com>.

Berzowska, Joey. "Second Skin and Soft Wear." Concordia Course Resources [online], Nov. 2003 [ret Nov. 22, 2003]. <http://hybrid.concordia.ca/~joey/classes/skin/rescources.html>.

Salkever, Alex. "The Many Shapes of Tomorrow's PC." BW Online [online], Nov. 4, 2003 <http://www.businessweek.com/technology/content/nov2003/tc2003114_2291_tc134.htm>.

(56) References Cited

OTHER PUBLICATIONS

Starner, Thad. "Human Powered Wearable Computing." 328 Appears IBM Systems Journal, vol. 35, No. 3 & 4 (Nov. 9, 1996).
Kerber, Ross, "Malden Mills' Next Hot Product: Fabrics That Heat Up," Boston Globe, Oct. 22, 2001, p. C4.
Sullivan, Andy, "PluggedIn: Cutting-Edge Science Creates Stain-Free Pants," Reuters, Jul. 27, 2003.
Claiming Infringement, Patent Owner of Computer Systems for Personalized Fashion Shopping Andrea Rose Files Suit Against Public Technologies . . . , Business Wire, Oct. 19, 1999.
Knapp, Louise, "3-D Eyes Turn to Fashion World," Wired News [online], Aug. 30, 2003 [retr. on Aug. 31, 2003]. Retr. from: <http://www.wired.com/news/culture/0,1284,60117,00.html>.
Sylvers, Eric, "In Milan, Working to Unfurl a High-Tech Blanket of Fiber," The New York Times [online], Nov. 3, 2003 [retr. on Nov. 3, 2003]. <http://www.nytimes.com>.
Nanowires Boost Plastic Circuits, Technology Review [online], Oct. 20, 2003 [retr. on Oct. 27, 2003]. Retrieved from: <http://www.technologyreview.com/articles/rnb_102003.asp>.
Brown, Chappell, "E-textiles, robot 'skin' among advances at IEDM," EE Times [online], Oct. 9, 2003 [retr. on Oct. 9, 2003]. <http://www.eetimes.com/story/OEG20031009S0028>.
The Pentacene Project, IBM Research / Projects / LEEM, Oct. 2003.
Heart Patients May Benenfit from Sensors in Clothes, Reuters, Oct. 8, 2003.
Product Concepts. Universal Display Corporation [online], Aug. 2003 [retrieved on Aug. 6, 2003]. Retrieved from the Internet: <URL: www.universaldisplay.com/concepts.php>.
Intellectual Property. Universal Display Corporation [online], Aug. 2003 [retrieved on Aug. 6, 2003]. Retrieved from the Internet: <URL: www.universaldisplay.com/ip.php>.
Cambridge Display Technology Fact Sheet, Cambridge Display Technology, Jul. 3, 2001.
Lindwer et al."Ambient Intelligence Visions and Achievements: Linking Abstract Ideas to Real-World Concepts." Proc. Conf. Design, Automation & Test in Europe (IEEE Mar. 2003).
Donev, Eugene, "Design and Implementing Organic Thin-Film Transistors (OTFTs)," Sep. 2002, 9 pgs., University of the South, Sewanee, Tennessee.
Nanomaterials, Soft Matter, and Electronic Materials Find Common Ground at 2003 MRS Spring Meeting, MRS Bulletin, Jul. 2003, pp. 517-534.
"Wearable Computing." MIT Media Lab / Human Design, Aug. 6, 2003.
DeVaul, et al., "MIThril: context-aware computing for daily life," White paper, Mass. Institute of Technology Media Laboratory (May 16, 2001).
Keyes, Edward, "The Enchantment Window Manager: A Wearable Computing User Interface," White paper, Mass. Institute of Technology Media Laboratory (Aug. 24, 2000).
De Vaul et al., "The Ektara Architecture: The Right Framework for Context-Aware Wearable and Ubiquitous Computing Applications," MIT Media Laboratory, 2000.
Starner, et al., "Visual Contextual Awareness in Wearable Computing." Perceptual Computing TR#465, MIT Media Laboratory (Sep. 22, 1998).
Sawhney, et al., "Nomadic Radio: Scalable and Contextual Notification for Wearable Audio Messaging," Proc. CHI'99 ACM Conf. on Human Factors in Comp. Sys. (May 15-20, 1999).
Clarkson, et al., "Auditory Context Awareness via Wearable Computing," MIT Media Laboratory, MIT Media Laboratory (Jan. 1, 1998).
Sawhney, et al. "Speaking and Listening on the Run: Design for Wearable Audio Computing," Proc. of the Second International Symposium on Wearable Computers (Oct. 1998), p. 108.
Healey, et al., "StartleCam: A Cybernetic Wearable Camera," Proceedings of the Second International Symposium on Wearable Computers (Oct. 1998), p. 42.
Colella, et al., "Participatory Simulations: Using Computational Objects to Learn about Dynamic Systems," in Proc. Computer Human Interface (CHI)'98 Conference (LA, Apr. 1998).
Schiele, Bernt, "DyPERS: A Dynamic Personal Enhanced Reality System," MIT Media Laboratory (Jul. 13, 1998).
Rhodes, Bradley J., "The wearable remembrance agent: a system for augmented memory," Personal Technologies Journal Special Issue on Wearable Computing, Personal Technologies, vol. 1 (1997), pp. 218-224.
Jebara, et al., "Stochasticks: Augmenting the Billiards Experience with Probabilistic Vision and Wearable Computers," in Proc. Int'l Sympos. on Wearable Computers (Oct. 1997).
Starner, et al., "Real-Time American Sign Language Recognition Using Desk and Wearable Computer Based Video," MIT Media Laboratory Perceptual Computing TR#446 (Sep. 17, 1998).
Sparacino et al., "Wearable Cinema/Wearable City: bridging physical and virtual spaces through wearable computing," in IMAGINA 2000 (Monte Carlo, Jan. 31-Feb. 3, 2000) pp. 17-20.
Rhodes, et al., "Wearable Computing Meets Ubiquitous Computing," Proceedings of the Third International Symposium on Wearable Computers (SF, CA, Oct. 18-19, 1999), pp. 141-149.
Sparacino, et al., "Technologies and methods for interactive exhibit design: from wireless object and body tracking to wearable computers," ICHIM99 (Sep. 22-26, 1999), p. 147.
Healey, et al., "Quantifying Driver Stress: Developing a System for Collecting and Processing Bio-Metric Signals in Natural Situations," Proc. Rocky Mt. BioEng.Sym (Apr. 1999).
Healey, et al., "A New Affect-Perceiving Interface and Its Application to Personalized Music Selection," Proc. 1998 Workshop on Perceptual User Interfaces (Oct. 10, 1998).
Starner, et al., "A Wearable Computer Based American Sign Language Recognizer," First International Symposium on Wearable Computers (ISWC '97) (Oct. 13-14, 1997), p. 130.
Tan, et al., "Tactual Displays for Wearable Computing," Personal Technologies, vol. 1 (Oct. 1997), pp. 225-230.
Picard, et al., "Affective Wearables," Personal Technologies, vol. 1 (Oct. 1997), pp. 235-240.
Healey, et al., "Digital Processing of Affective Signals," Proceedings of the IEEE International Conference on Acoustics, Speech, and Signal Processing (May 12-15, 1998).
Roy, et al, "Wearable Audio Computing: A Survey of Interaction Techniques," MIT Media Laboratory Perceptual Computing Group TR#434 (Apr. 1997).
Mann, Steve, "Wearable Computing: A First Step Toward Personal Imaging," Computer, vol. 30, No. 2 (Feb. 1997), pp. 25-32.
Starner, et al. "Augmented Reality Through Wearable Computing," Presence: Teleoperator and Virtual Environments, vol. 6, No. 4 (Aug. 1997) pp. 386-398.
Rhodes, et al., "Remembrance Agent, A continuously running automated information retrieval system," Proceedings of the First International Conference on the Practical Application of Intelligent Agents and Multi Agent Technology (PAAM '96), Apr. 22-24, 1996, Westminster Central Hall, London, UK (1996), pp. 487-495.
Mann, Steve, "Mediated reality," MIT Media Laboratory Perceptual Computing Section Technical Report No. 260 (Dec. 1994).
Picard, R.W., "Affective Computing," M.I.T. Media Laboratory Perceptual Computing Section Technical Report No. 321 (Nov. 26, 1995).
Starner, Thad, "The Cyborgs are Coming or the Real Personal Computers," MIT Media Laboratory Perceptual Computing Section Technical Report No. 318 (1994).
Sawhney, et al., "Design of Spatialized Audio in Nomadic Environments," in Proceedings of the Fourth International Conference on Auditory Display (ICAD97) (Nov. 2-5, 1997).
Schwartz, et al. "The Smart Vest: Towards a Next Generation Wearable Computing Platform," M.I.T. Media Laboratory Perceptual Computing Section Tech. Report No. 504 (Jul. 1999).

\* cited by examiner

RECONFIGURABLE GARMENT DEFINITION AND PRODUCTION METHOD

RELATED U.S. APPLICATION DATA

This is a continuation application of U.S. application Ser. No. 13/454,390, originally filed on Apr. 24, 2012, which is a continuation application of U.S. application Ser. No. 12/540,954 originally filed on Aug. 13, 2009, which is a continuation of U.S. application Ser. No. 12/238,336 originally filed on Sep. 25, 2008, which is a continuation application of U.S. application Ser. No. 11/027,819 filed on Dec. 29, 2004.

FIELD OF INVENTION

Invention relates to computer-assisted methods and systems for novel garment design and manufacture, particularly automated using software, databases and related electronic networks and sensors.

BACKGROUND OF INVENTION

Conventional fashion industry employs various creative manual processes to design and produce new clothes. However conventional techniques are limited to the extent that garment design and production processes are not easily customized, time-constrained, and are not easily reconfigurable. For example, customer has to wait at cashier, try various kinds of clothes in a changing room, take a lot of measurements, inaccurately customize the garment, or buy standardized garment to speed-up the purchasing process.

Accordingly, there is a need for improved definition and production efficiency by using some electronic automation techniques, for example, to assist prototype design, garment customization, and garment grading. Furthermore to increase customer satisfaction guarantee of manufactured garment, novel computer-aided methods for customers to input their body-profile information and view their appearance with designed garment are presented unobviously herein.

SUMMARY

Computer-aided design and manufacture software and/or hardware automates garment and fashion definition and production. Configurable garment and fashion system includes ornamental element, pattern display, and personal identifier and wireless sensor electronics, effectively integrating the business world of fashion and consumer electronics.

Computer-supported process especially configured for user easily to design reconfigurable apparel, input body-profile information, input assembly and test preferences, receive and give recommendation whether the garment fits the body profile to assist user in making a purchasing decision. Information resulting from the process can be protected and are accessible by pre-determined user.

Optionally fabric or garment with integrated flexible information infrastructure and electrode/sensors, methods of representing customer body-profile information in various formats, and methods for assisting a customer to select properly-sized apparel may be used herein.

Generally electronic process assists customer directly to design customized garment with help of either human or computer fashion advisor. Thus invention resembles virtual store with a fashion advisor. User can confidently design and purchase garment conveniently.

BRIEF DESCRIPTION OF FIGURES

The accompanying drawings which are incorporated in and form a part of this specification, illustrate embodiments of the invention and together with the description, serve to explain the principles of the invention.

DETAILED DESCRIPTION

Reference is made in detail to the preferred embodiments of the invention. While the invention is described in conjunction with the preferred embodiments, the invention is not intended to be limited by these preferred embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, the invention may be practiced without these specific details. In other instances, various garments, design or manufacturing methods, automated procedures, reconfigurable components, software or database applications, network systems, and electronic or optical circuits have not been described in detail so that aspects of the invention will not be obscured.

Figure 1:
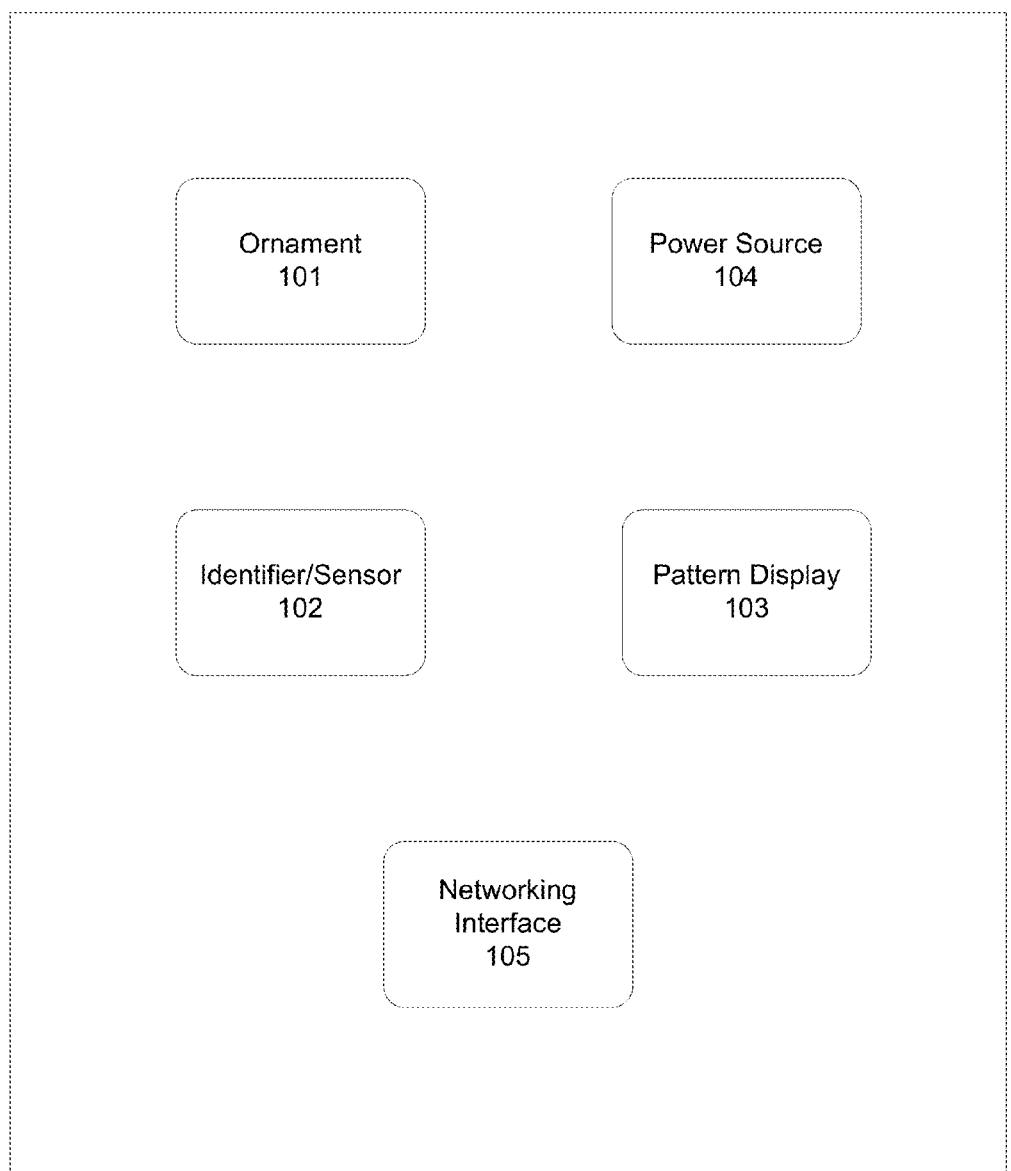
FIG. 1 is a diagram representing a simplified configurable garment according to an embodiment of the present invention.

FIG. 1 is a simplified diagram showing representative configurable garment 100 according to an embodiment of the present invention. As understood herein, the term "garment" is interpreted and construed broadly to mean any wearable item and/or accessory, such as shirt, pant, jean, slack, shorts, skirt, khaki, glasses, shoes, scarf, jacket, tie, belt, socks, wallet, umbrella, etc. Garment may be knitted, molded, photo-lithographically deposited or constructed using one or more masking or implanting steps or otherwise made using one or more organic, synthetic, conductive, semiconductive or insulated filament, fabric, fibres, polymers, carbon nano-fibers, pentacene, thin-film transistors, semiconductor substrate, etc.

Garment 100 comprises one or more active or passive, smart or intelligent, personalizable, tailorable, programmable or configurable electronic, mechanical or optical logic device or finite state machine, gate array, cross-bar, transmission-line, antenna, multiplexer, demultiplexer, modulator, amplifier, analog-to-digital/digital-to-analog converter, interconnect, microprocessor, controller, thermostat, thermometer, sensor, transponder, radio-frequency identifier or tag (RFID), accelerometer, piezoelectric detector, transistor, diode, resistor, capacitor, inductor, switch, latch, flip-flop, such as ornament or jewelry 101, user identifier and/or sensor 102, input/output pattern display 103, power source 104 and networking or communication interface 105.

Ornament 101 comprises one or more ornamental or functional electronic device or module incorporated into garment 100, including music or media player or recorder, global positioning or navigational location system, antenna or wireless transceiver, mobile phone or radio communicator, computer or processor, television or video appliance, alarm or emergency indicator, video or image camera, communication switch or networking connection, or electroluminescent lamp or display. Ornaments 101 may be washable or detachable.

Ornaments 101 may enable garment 100 to function as interface to control remotely or programmably various electronic device, e.g., jacket interfacing with light switches or television remote control. For example, ornament 101 may functionally disregard or effectively filter chemical substances or other harmful electromagnetic energy rays that can cause cancer or other disease, thereby reducing risk or cause of bio/chemical terrorism or nuclear threat.

Ornament 101 also may be composited to enable garment and fashion 100 to be stain-free, therefore not requiring use of detergent and materially enhance environmental quality. Ornament 101 may also be composited to provide that clothes do not contain disease, and are safe from HIV/AIDS and other diseases. Optionally, ornament 101 may play music, video or other media recording or enable multi-party voice or video communication based on user emotion detected by human-emotion detector effectively integrated in garment 100. Ornament 101 may be electronically-controlled dispenser or vial for releasing selectively one or more fluids or gases, such as perfume, medicine, food/drink, pheromone, etc. according to user, processor or software instruction.

Sensor 102 comprises one or more identifier or sensor device integrated with garment 100. Identifier uniquely recognizes and identifies particular user with one or more alphanumeric, coded, or signature pattern. Sensor 102 may comprise one or more medical or physiological bio-chemical sensor, temperature or heat sensor, optical or infrared sensor, accelerometer, electromagnetic sensors, human-emotion detector, pollution-rate detector, water condition or quality sensors, motion sensor, microphones or media detector, weight scale, etc. Such medical sensors may measure physical information such as heart rate, blood pressure, blood sugar level, and other vital signs and effectively detect and diagnose diseases such as HIV/AIDS, cancer, etc.

Sensor 102 may detect weapons, bombs, or other military equipment particularly for safety-inspection purpose. Sensor 102 can be integrated inconspicuously into garment 100. Sensor 102 or ornament 101 may provide or effectively resemble ambient intelligence, i.e., invisible, present whenever user needs it, enabled by simple and effortless interaction, or autonomously acting adaptively to user and context.

Pattern display 103 comprises graphical or media communication interface, e.g., organic light emitting device (OLED), flexible optical fiber screen or communication fibers coupled or woven into clothes capable of up/downloading data and signals, and providing or displaying graphics such as video, logos, texts, patterns, and images directly onto clothes or surfaces coupled thereto. Based on wireless radio signals or electrical commands, pattern display 103 may change color, images, projections, and patterns using electrical power provided by power source 104. Pattern display 103 also offers access to network or online services such as internet, video, and e-commerce as well as displays sensor 102, power source 104 or ornament 101 status or data.

For example, sporting clothes monitor heart rate, blood pressure, temperature, respiration rate or other physiological metric during gym workout or exercise for display on pattern display 103, or pattern display 103 of clothing fitted with global positioning system worn by skiers or mountaineers displays geographic location. Sensor 102 and pattern display 103 may be distributed regularly in grid or other pattern.

Power source 104 generates, provides or accesses electrical power for garment 100, and comprises AC/DC source, electromechanical generator, portable rechargeable battery, fuel cell, environment heat source, mechanical source, light source, or other energy source for providing electrical power. Environmental heat source may be produced by tapping or collecting natural heat given-off by user body; mechanical heat source is produced by transforming mechanical energy of user movement into electrical power; and optical heat source is produced by transforming surrounding light into electrical power. Use of environmental heat source, mechanical heat source or optical heat source as power source 104 reduces regular battery usage, and therefore materially enhance quality of the environment.

Garment 100 optionally employs heat sink to reduce heat trapped inside clothes, so that garment 100 has more efficient utilization and conservation of energy resources provided by power source 104.

Networking interface 105 communicates via electromagnetic wireless radio-wave signals or wired interconnected network to provide garment 100 internal and/or external communications with user and database. Flexible or rigid conductive or semi-conductive fibers are woven into garment 100 to transmit/receive signals inside garment 100. Conductive fibers may be interwoven with material of garment 100, or added thereto in narrow strips of ribbon or patterned portions that are sewn at user-specified or predefined places. Garment 100 may be made from electro-textile material, e.g., using yarns made of synthetic or metallic fibers for knitting into cotton or polyester. Yarn fibers may be clad with metal, silver, nickel or other metallic or conducting material, and then optionally insulated with polymer or other insulator or dielectric. Conductive fibers are connected to power source 104 to provide circuits as defined herein.

Networking interface 105 allows user selectively in real-time to control or program ornament 101, sensor 102, pattern display 103, and power source 104 through user data input devices such as touchpad, voice recognition tool, keypad, etc. Networking interface 105 may couple garment 100 with user interface appliance 300, assembly source 407 or database 403. For example, networking interface 105 sends identifier/sensor 102 data, power source 104 status data, or pattern display 103 information to database 403, and receives electrical commands or other control signals from assembly source 407. Garment 100 may comply with applicable governmental or regulatory requirement or rule, as proven by testing, quality or other conformation process.

For example, garment 100 may be attached or coupled to motorized frames where disabled individuals can wear such garment 100 to help such individuals walk, climb steps, etc. Battery-powered plastic frame attached to garment 100 relies on electrodes attached to garment 100 detecting from skin motor nerve signals emitted by the brain before instructing muscle cells to contract, thereby providing real-time instruction for frame to move synchronously with user.

In another example, sensor 102 embedded in garment 100 provides military, security or surveillance functions. Optical fibers and special sensors inside garment 100 may detect bullet wounds and monitor body vital signs during combat or other danger conditions. Sensor 102 embedded in carpets, wallpapers and various kinds of canvas covers additionally detects unrecognized person facial image or voice pattern.

Yet in another example, doctors may design, configure or provide customized garment 100 for patients. Sensor 102 printed or provided on fabric allows doctor to monitor patients without having to keep them physically in hospital. Networking interface 105 transmits/receives sensor 102 data with doctor or hospital computer, or sounds alarm if sensor 102 senses patient problem or danger condition. Further sensor 102 applications enable garment worn to medicate or diagnose disease.

Effectively cutting or tailoring such electronic cloth according to personalized design size or shape may result in difficulty to make good physical or electrical signal connections between different parts of same garment 100, and may be solved by manufacturing seamless clothing, to avoid cutting and stitching problem altogether. Preferably security or privacy of personal garment 100 design and manufacturing files and confidential information are maintained.

Figure 2:
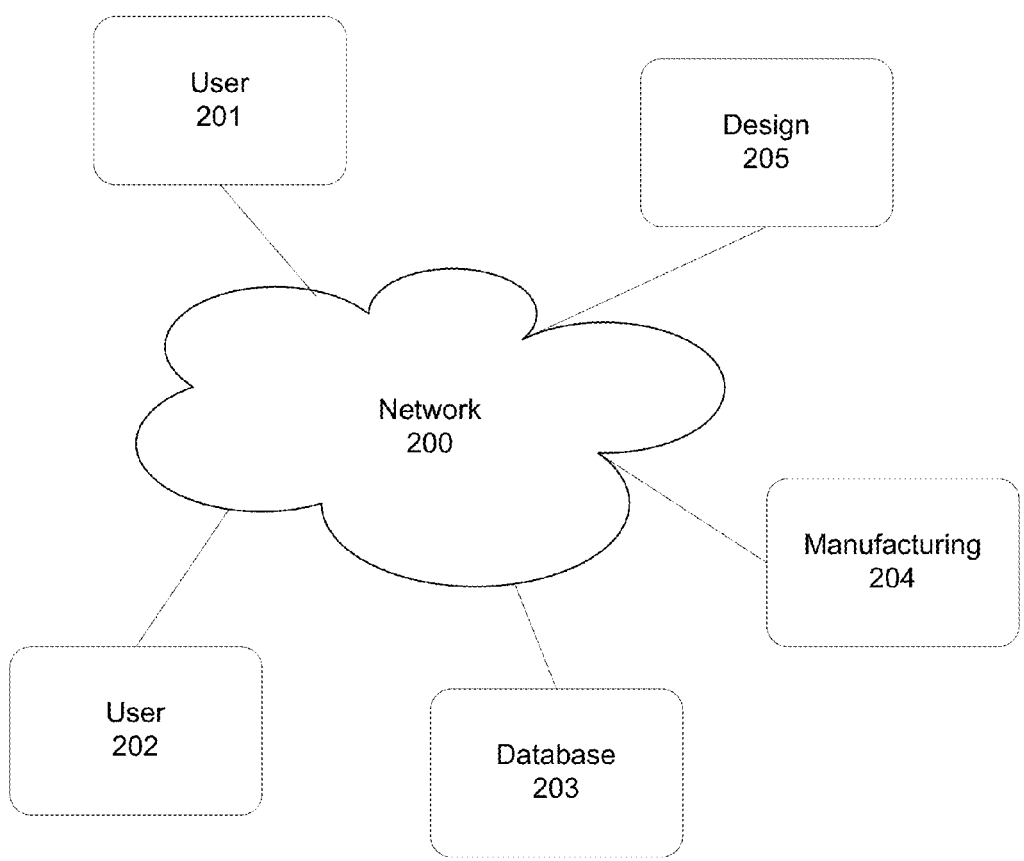
FIG. 2 is a generalized diagram of network system according to an embodiment of the present invention.

FIG. 2 diagram shows digital communication system interconnecting local or wide-area network accessible devices, hosts, computers, servers, or other processor and/or storage, such as user 201, memory or storage 203, design processor 204, and manufacturing processor 205. User 201, 202 may access or store information stored in storage 203 through network 200. Design source 204 runs design process as controlled by user 201 and manufacturing source 205 runs manufacturing or testing process locally or globally; there are no limitations on network-access geographic location.

Figure 3:
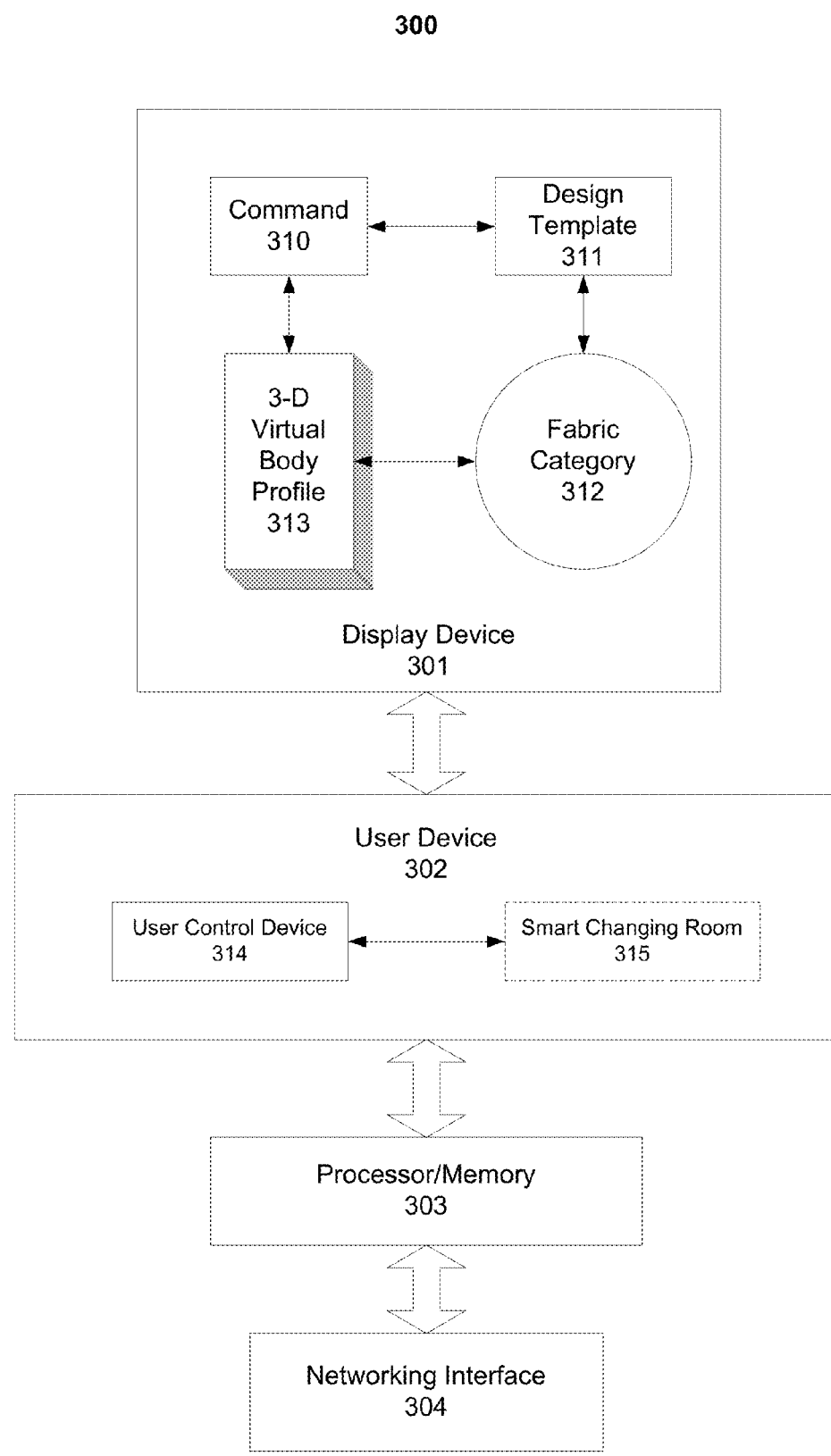
FIG. 3 is a diagram showing appliance system according to an embodiment of the present invention.

FIG. 3 diagram shows user interface appliance 300 according to an embodiment of the present invention. Appliance 300 comprises display device 301, user device 302, memory/processor 303, and networking interface 304.

User interface appliance 300 employs Graphical User Interface (GUI); as understood herein, the term "GUI" is interpreted and construed broadly to mean any graphical, audio, video or other media display or sensing system for communicating digital or analog input and/or output of one or more program or function, e.g., presenting icons or objects, buttons or selections, dialogue boxes or windows, on-screen in two or three dimensions. User interface appliance 300 has program known as user interface appliance 300 program that allows GUI to receive information or profile selection from users 201 202, display or modify garment design, display actual or virtual 3-D user body profile with or without wearing garment 100, process, analyze, recommend and store information, and communicate with network 200. User interface appliance 300 can be accessed anywhere, at store or through internet 200.

Display device 301 comprises electronics display or media communication device having image-displaying region providing visual representation of objects or other relevant garment attributes from user interface appliance 300 program and user interactions or selections with user interface appliance 300 program. Display device 301 preferably comprises command 310, design template 311, fabric category 312, and 3-D virtual body profile 313.

Command 310 comprises icons, buttons and dialogue boxes that represent user communication with user interface appliance 300. Command 310 is coupled with user tool 302 to display user interaction with user interface appliance 300 program. Through command 310, user chooses a variety of options when configuring garment 100 definition. As understood herein, the term "garment definition" is interpreted to mean any garment attribute, parameter or property, e.g., design style, fabric category, functional property, etc.

Various design options, parameters or features may be selectably combined in same garment 100, including, but not limited to, motion capture sensor, phosphorescent element, thermo-electric sensor, electro-adhesive element, variable color element, variable shade element, water shedding, bio-monitor sensor, electroluminescent element, sound emitting/capturing element, variable opacity element, video display, force feedback element, optical chameleon element, photoelectric element, computational array, self-repairing element, touch sensitive element, toxin filtering element, voice recognition software, wireless communication device, variable rigidity element, variable shape element, variable reflectivity element, thermal chameleon element, self-cleaning element, etc.

User maybe also be enabled to choose pre-configured templates, parameters or customized configuration for work/leisure outfit, dance-club gear, immersive media suit, covert-operations bodysuit, adventure climber, exploration suit, backpack, utility vest, ultra tarpaulin; each application preferably associated with pre-configured garment design, parameter or feature options.

User can select or define available garment material or size by interacting with command 310. User is also guided to design architectural garment by providing or selecting functional property of garment 100, e.g., choosing garment 100 that transforms into tent, raincoat, massage chair, furniture, mattress, or medical wheelchair.

Design template 311 may provide available choices of design template and/or user current selection of design template. As understood herein, the term "design template or style" 311 is interpreted and construed broadly to mean any fashion design element, parameters or clothing application, e.g., shirts style or size, collar design, pocket style or size, neck style, back detail, sleeve detail or length, cuffs, monograms, shirt fit, shirt size, shirt tail, stitching, tie space, etc.

Design template may employ one or more adaptive, neural, fuzzy, Bayesian, or other intelligent control or programming method or algorithm to apply or design one or more garment elements or parameters according to one or more predefined or stored user or expert rule sets, preferably tailoring or weighing one or more design factors according to user-specific conditions or preferences. Additionally design template may include or consider personal user objective and/or objective indications, preferences, style, range, degree, socio/political affiliation, e.g., conservative, liberal, moderate, republican, democrat, heterosexual, homosexual, bisexual, catholic, protestant, jewish, muslim, etc.

Fabric category 312 provides choices of fabric category available and/or user current selection of fabric category. As understood herein, the term "fabric category" 312 is interpreted and construed broadly to mean any material category such as patterns, material, color, stripes, solids, checks, texture, etc.

Once user control device receives specific command from user, user interface appliance 300 program may combine command 310, design template 311, and/or fabric category 312 information into garment definition. User can add further information to garment definition and generate garment test script with aid of verification source 404. For example, garment may be purchased below price range, or testing process is focused on biomedical sensor functionality.

Three-dimensional virtual body profile 313 comprises image-processing device for displaying 3-D replica or simulation model based on body profile information. Receiving command from user, 3-D virtual body profile 313 displays 3-D representation of body profile information with or without being superimposed by designed garment 100. Three-dimensional virtual body shop 313 is coupled with verification source 407, thereby enabling 3-D virtual body shop 313 to display replica wearing recommended garment.

User device 302 comprises user control device 314 or smart changing room 315. User control device 314 comprises mouse, joystick, keyboard, touchpad, or speech recognition software allowing user to control user interface appliance 300 program. For example, user moves pointer on screen (controlled by mouse), selects certain objects by pressing buttons on mouse while pointer is pointing thereto, touches or presses objects on display screen 301 to control program, inserts text using keyboard and verifies information using speech-recognition tool.

User control device 314 allows user to key-in codes and fetch personalized garment definition to be displayed onto display device 301. User control device 314 can modify 3-D body representation, such as modifying height and adjusting relative color contrast of image and modify garment property displayed on display device 301. User who has body profile stored in computer-readable storage devices like flash memory, card, tag or disks may let user control device 314 read information and send to 3-D virtual body profile 313.

Optionally user tool 302 comprises device to obtain person body profile information, smart changing room 315. Smart changing room 315 comprises fixed or movable cameras distributed at convenient points around room for measuring and/or extrapolating three-dimensional replica of user. Various body profile parameters of body profile information are measured according to image captured. Resulting data is then saved by processor/memory 303 and fed into user interface appliance 300 program, which then transfers such information to 3-D virtual body profile 313. Three dimensional virtual body profile 313 such uses data to display 3-D replica of person with or without wearing designed garment and fashion 100.

Multiple-angle images are provided to enable system to measure or calculate parameters of user body profile, such as chest size, waist size or hip size. If movable cameras capture continuous pictures, playback of body profile is used to combine animated garment images to provide motion effect. System may require manual assistance to obtain accurate result. Alternately body profile information refers to captured digital image, such as photograph or video.

To increase quality of recommendation received, user is encouraged to input more physical information, such as eye colors, eye shape, hair shape or color, skin color, face shape, height, body shape, shoulder line, etc. Users can input their sizes (e.g., collar, waist, hip, yoke, inseam, thigh, skirts length, shorts length, knee length, ankle length, cuff lengths, etc.) or height and/or face structure. User may use manual or electronic method to enter information.

Multiple users may access same garment definition or template, however each user may customize or tailor such template according to personal measurements, preferences, style, etc. (e.g., "Megan" customer may prefer feminine youth size 10 in pink or lavender, and "Jared" customer may prefer masculine youth size 8 in blue or green.) If such information is proprietary, then permission or licensing of particular user may be required to proceed.

Processor/memory 303 comprises information module for storage and/or retrieval of information about user (such as account information, previous design templates, etc.), allowing user interface appliance 300 to be used by one or more users. Processor/memory 303 may receive information from remote database or storage devices storing library of garment definition. For example, database 403 provides detailed information of saved template required by user, database 403 provides stored body template as requested by user, user requiring specific billing plan may require database to provide detailed explanation of plan and his/her financial information, user requiring regulatory check may require database to provide regulatory information, user requiring that assembly and testing process take place at location require database to provide location information to user.

User can easily reconfigure garment 100 design before or after receiving recommendation from verification source 407. Recommendation from verification source can be displayed by 3-D virtual body shop 313, spoken by speech tool of user control tool 314, or displayed by display screen 301.

Figure 4:
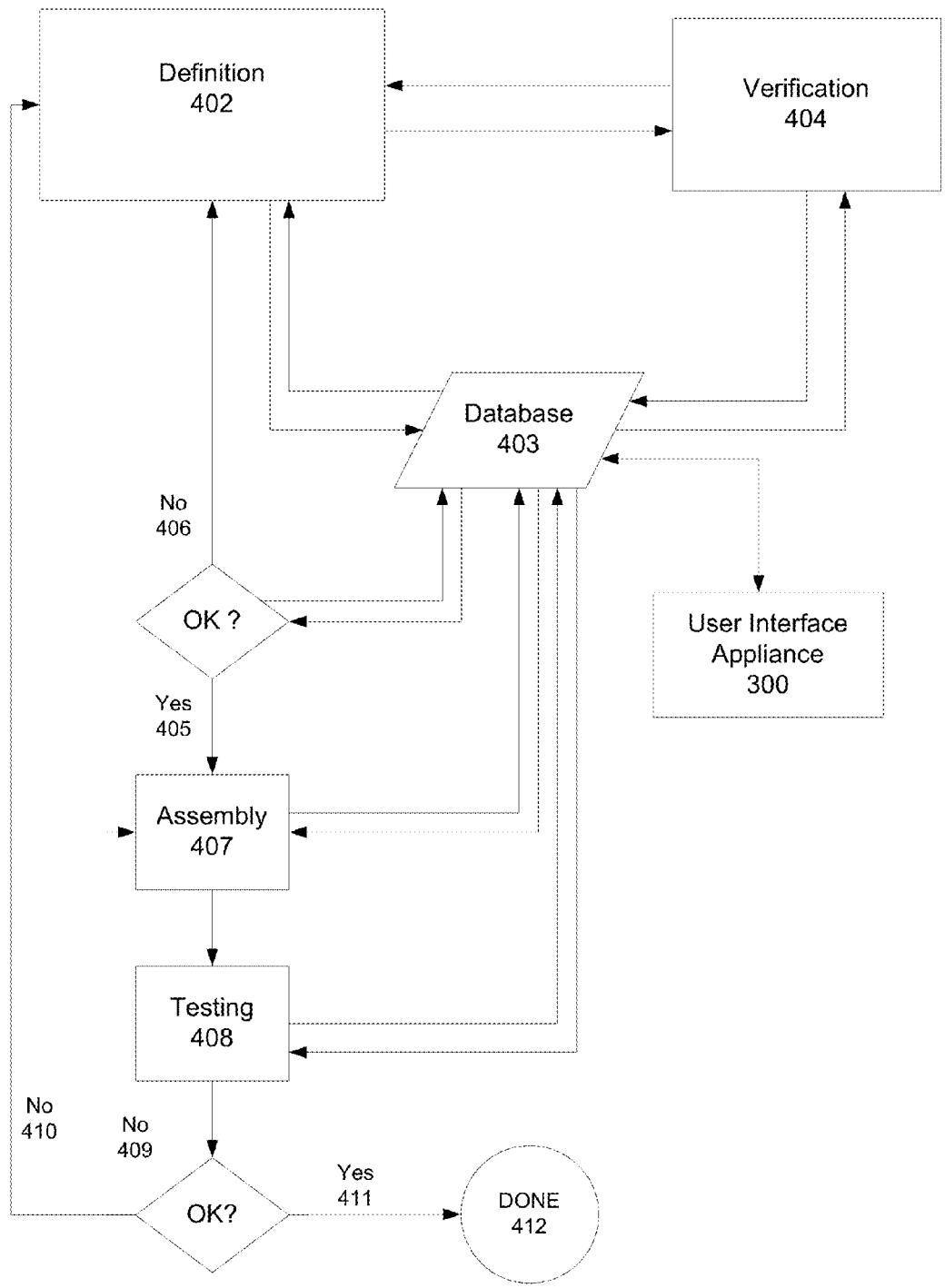
FIG. 4 is a flow diagram illustrating novel garment and fashion design and manufacturing process according to an embodiment of the present invention.

FIG. 4 flow diagram illustrates garment design and/or manufacturing method according to an embodiment of the present invention. In definition process, user interface appliance 300 sends garment definition or design file to database 403, which transfers information to definition source 402. Garment definition or design file includes garment property or other information specified by user, such as price range, governmental regulation, occupation, etc. User can reset or stop process at any time.

Referring to verification process, definition source 402 sends garment definition with other information to verification source 404. Verification process may be done by one or more fashion and regulatory experts or by computerized garment grading system. Verification source 404 checks regulatory requirements including environmental policy. Verification source 404 optimizes cost of product by selecting appropriate or low-cost garment material or assembly location. Verification source 404 checks whether cost of designed garment 100 meets user requirement. Verification source 404 is reconfigurable computer software that gives recommendation based on fashion trends determined by user input. Verification source 404 as a computerized fashion or expert consultant programmed to comment on user apparel selection acts as fashion advisor and provides fashion style recommendation. Verification source 404 checks whether garment definition meets functionality requirement determined by user.

Verification source 404 sends resulting information to database 403, which sends to user interface appliance 300 for user confirmation. If user requires no additional process 405, information or design file is sent to assembly source 407, else 406 proceed back with definition process 402.

Assembly source 407 using design file proceeds with manufacturing process. After manufacturing process is done, manufacturing information is sent to database 403. Testing source 408 receives piece of garment 100 from assembly source 407 and garment test script from database 403. Testing source 408 runs test process and sends test result to database 403, which transfers information to user through user interface appliance 300. If user requires no additional process 411, garment sent to user 412; else 409 goes back to assembly process 407 or 410 goes back to definition process 402.

Generally computer-assisted method and system automatically or interactively configures or tailors garment or fashion design. Preferably one or more user or subscriber template or definition is completed, modified, accessed or re-used to determine user or user-group garment profile or requirements. Thus in automated manner one or more garment-design file(s) is generated by computer or software program for configuring or reconfiguring a reconfigurable or programmable garment or prototype thereof, preferably according to predefined, select or full portion of the user garment profile.

Also reconfigurable garment prototype may be configured according to one or more expert or fashion design template, which is provided in one or more template library including various design templates. Completed user template is accessible remotely through a digital network or Internet using user-secured biometric authorization or garment-design usage license or script.

Optionally expert design template is accessible remotely through digital network using a garment-design usage license, such that a user of the reconfigurable garment prototype is financially charged for actual usage of the reconfigurable garment prototype configured according to the expert design template. Expert design template provides celebrity, fashion expert, or other famous designer preferences, definition, style or other fashion look-and-feel uniquely or identifiably pertaining to garment design, composition, presentation, fit or manufacture thereof. Expert design template parameters may be selectively modulated, tuned or balanced against or relative to user template parameters.

Reconfigurable garment prototype may include electrically one or more reconfigurable logic circuit that is programmable according to the garment-design file, as well as include one or more sensors for sensing user condition, thus enabling the reconfigurable garment prototype to be reconfigured according to a change in user condition. Additionally reconfigurable garment prototype may include one or more media or communication interface for providing or receiving audio/visual content or signal programmably according to the garment-design file.

Preferably garment design file is generated using a software simulation application for modeling the reconfigurable garment prototype virtually according to select portion of the user garment profile. Optionally modified garment-design file is generated for reconfiguring remotely the reconfigurable garment prototype according to a modified user template or a modified expert design template.

Foregoing descriptions of specific embodiments of the invention have been presented for purposes of illustration and description. They are not intended to be exhaustive or to limit the invention to the precise forms disclosed. Modifications and variations are possible in light of the above teaching. Various novel embodiments to present endorsement scheme include, for example: digital network security or energy checking in residential, business, educational, or other working system context wherein one or more network-connected participants may endorse electronically in response to certain security-checking proposal according to present novel scheme; entertainment, theatrical, sports, or other broadband or media system context wherein one or more network-connected performer, staff or audience member may endorse electronically in response to certain live interactive proposal according to present novel scheme; and medical or healthcare system context wherein one or more network-connected patient, doctor, nurse or other staff may endorse electronically in response to certain medical diagnosis, interview, or other healthcare dialog according to present novel scheme.

The embodiments were chosen and described in order to explain the principles and the application of the invention, thereby enabling others skilled in the art to utilize the invention in its various embodiments and modifications according to the particular purpose contemplated. The scope of the invention is intended to be defined by the claims appended hereto and their equivalents.

The invention claimed is:

1. Electronically reconfigurable sleeve or cuff garment comprising:
an electronically personalizable sleeve or cuff garment comprising a flexible optical fiber screen woven into the sleeve or cuff, a media player, and an identifier device;
a user interface appliance comprising a user device, a processor/memory, and a networking interface; and
a power source;
wherein the networking interface is to couple with the user interface appliance with the sleeve or cuff garment using reconfigurable software to configure operation of the media player enabling real-time user-control via the user device and the flexible optical fiber screen, the software further configuring electronically a variable color element, a variable reflectivity element, a variable electroluminescent element, or a variable optical chameleon element of the flexible optical fiber screen according to a computerized celebrity or fashion expert consultant application that automatically generates a fashion or style recommendation using a design template for personalizing the sleeve or cuff garment electronically according to a user-defined garment definition or user input via the user device, thereby allowing the sleeve or cuff garment to change color, images, projections, and patterns based on configuration commands for a unique fashion look-and-feel and for displays of texts, data, and audio and video media content.

2. The garment of claim 1 wherein the user device further comprises a touchpad to allow real-time user-control of the garment, and a user control device to read data from computer-readable storage devices, the identifier device comprising a radio-frequency identification device (RFID) coupled to a global positioning system (GPS) device for wirelessly locating the garment, the media player further comprising a memory or storage device and a wireless communicator to download media from a network via the networking interface and to store in the memory or storage device, usage of the media downloaded being financially billable to user according to information in the identifier device, the power source comprising an optical heat source produced by transforming light into electrical power.

3. Electronically reconfigurable sleeve or cuff garment comprising:
an electronically reconfigurable sleeve or cuff garment comprising a programmable appliance comprising a pattern display, a media player, an identifier device, a user interface, a processor, a networking interface, and a power source;
wherein the networking interface is to couple with the user interface using reconfigurable software executable by the processor to configure operation of the media player enabling real-time user-control via the user interface, the software reconfiguring the pattern display via a variable color element, a variable reflectivity element, a variable electroluminescent element, or a variable optical chameleon element according to a computerized celebrity or fashion expert consultant application that automatically generates a fashion or style recommendation using a design template for personalizing the sleeve or cuff garment electronically according to a user-defined garment definition or user input via the user interface, thereby allowing the sleeve or cuff to change color, images, projections, or patterns based on configuration commands for a unique fashion look-and-feel and for displays of texts, data, and audio or video media content.

4. The garment of claim 3 wherein the user interface further comprises a touchpad to allow real-time user-control of the garment and a user control device to read data from at least one computer-readable storage device, the identifier device comprising a radio-frequency identification device (RFID) or a global positioning system (GPS) device for wirelessly locating the garment, the media player further comprising a storage device and a wireless communicator to download media from a network via the networking interface and to store in the at least one storage device, usage of the media downloaded being financially billable to user according to information in the identifier device, the power source transforming light into electrical power.

5. The garment of claim 3 wherein the software causes one or more hardware reconfigurable logic circuit or software simulation model accessible by the processor in the garment to be reconfigured electronically according to a change in a sensed user condition, thereby such software adaptively enabling reconfigured garment personalization via automated stylistic reconfiguration of garment prototype according to computerized fashion advisor or expert consultant design recommendation.

6. Electronically reconfigurable wrist, sleeve or cuff garment comprising:
an electronically reconfigurable sleeve or cuff wearable on a user wrist comprising a programmable appliance comprising a pattern display, a media player, an identifier device, a user interface, a processor, a networking interface, and a power source;
wherein the networking interface is to couple with the user interface using reconfigurable software executable by the processor to configure operation of the media player enabling real-time user-control via the user interface, the reconfigurable software reconfiguring the pattern display via a variable color element, a variable reflectivity element, a variable electroluminescent element, or a variable optical chameleon element according to a computerized celebrity or fashion expert consultant application that automatically generates a fashion or style recommendation using a design template for personalizing the sleeve or cuff garment electronically according to a user-defined garment definition or user input via the user interface, thereby allowing the sleeve or cuff garment to change color, images, projections, and patterns based on configuration commands for a unique fashion look-and-feel and for displays of texts, data, and audio or video media content;
wherein the user interface further comprises a touchpad to allow real-time user-control of the garment and a user control device to read data from one or more computer-readable storage devices, the identifier device comprising a radio-frequency identification device (RFID) or a global positioning system (GPS) device for wirelessly locating the garment, the media player further comprising a storage device and a wireless communicator to download media from a network via the networking interface and to store in such storage device, usage of the media downloaded being financially billable to the user according to information in the identifier device;
wherein the reconfigurable software causes one or more hardware reconfigurable logic circuit or software simulation model accessible by the processor in the garment to be reconfigured electronically according to a change in a sensed user condition, thereby such software adaptively enabling reconfigured garment personalization via automated stylistic reconfiguration of a garment prototype according to computerized fashion advise or expert consultant design recommendation.

7. Electronically reconfigurable wrist, sleeve or cuff garment comprising:
an electronically reconfigurable sleeve or cuff wearable on a user wrist comprising a programmable appliance comprising a pattern display, a media player, an identifier device, a user interface, a processor, a networking interface, and a power source;
wherein the networking interface is to couple with the user interface using reconfigurable software executable by the processor to configure operation of a force feedback element, the force feedback element serving as signal of notification for the garment user, the signal of notification being generated by the reconfigurable software or delivered to the electronically reconfigurable wrist, sleeve or cuff garment from a network via the networking interface according to a computerized celebrity or fashion expert consultant application that automatically generates a fashion or style recommendation using a design template for personalizing the sleeve or cuff garment electronically.

8. The garment of claim 7 wherein the force feedback element is generated in response to a signal originating from a second electronically reconfigurable wrist, sleeve or cuff garment, the signal being transferred to from the first electronically reconfigurable wrist, sleeve or cuff garment from the second electronically reconfigurable wrist, sleeve or cuff garment via the networking interface.

9. The garment of claim 7 wherein the force feedback element is generated in response to an emergency notification signal, the emergency notification signal being delivered from a network via the networking interface.

10. The garment of claim 7 wherein the user interface further comprises a touchpad to allow real-time user-control of the garment and a user control device to read data from at least one computer-readable storage device, the identifier device comprising a radio-frequency identification device (RFID) or a global positioning system (GPS) device for wirelessly locating the garment.

11. Method for electronically reconfiguring a wrist, sleeve, or cuff garment comprising:
a network interface interacting with the user interface of an electronically reconfigurable wrist, sleeve, or cuff garment using a reconfigurable software; the wrist, sleeve or cuff garment comprising a programmable appliance comprising a pattern display, a media player, an identifier device, a user interface, a processor, a networking interface, and a power source;
the software reconfiguring the pattern display via a variable color element, a variable reflectivity element, a variable electroluminescent element, or a variable optical chameleon element according to a computerized celebrity or fashion expert consultant application that automatically generates a fashion or style recommendation using a design template for personalizing the sleeve or cuff garment electronically according to a user-defined garment definition or user input via the pattern display or the user interface, thereby allowing the sleeve or cuff to change color, images, projections, and patterns based on configuration commands for a unique fashion look-and-feel and for displays of texts, data, and audio and video media content.

12. The method of claim 11 wherein the user interface further comprises a touchpad to allow real-time user-control of the garment and a user control device to read data from one or more computer-readable storage devices, the identifier device comprising a radio-frequency identification device (RFID) or a global positioning system (GPS) device for wirelessly locating the garment, the media player further comprising a storage device and a wireless communicator to download media from a network via the networking interface and to store in such storage device, usage of the media downloaded being financially chargeable to user according to information in the identifier device.

13. The method of claim 11 wherein the software causes one or more hardware reconfigurable logic circuit or software simulation model accessible by the processor in the garment to be reconfigured electronically according to a change in sensed user condition, thereby such software adaptively enabling reconfigured garment personalization via automated stylistic reconfiguration of garment prototype according to computerized fashion advise or expert consultant design recommendation.

14. A network for transferring data between electronically reconfigurable wrist, sleeve or cuff garments comprising:
   a plurality of servers;
   one or more electronically configurable wrist, sleeve or cuff garments;
   a network interconnecting said servers to said electronically reconfigurable wrist, sleeve or cuff garments;
   wherein the network allows for the dynamic, remote and wireless transfer of data between an electronically reconfigurable wrist, sleeve or cuff garment and a server;
   wherein at least one of said wrist, sleeve or cuff garment accesses via the network a computerized celebrity or fashion expert consultant application that automatically generates a fashion or style recommendation using a design template for personalizing the sleeve or cuff garment electronically.

15. Electronically reconfigurable wrist, sleeve or cuff garment comprising:
   an electronically reconfigurable sleeve or cuff wearable on a user wrist comprising a programmable appliance;
   wherein the programmable appliance accesses reconfigurable software executable by a processor to configure wearable operation uniquely according to a computerized celebrity or fashion expert consultant application that automatically generates a fashion or style recommendation using a design template for electronically personalizing the sleeve or cuff garment.

* * * * *